(12) United States Patent
Pokrovski et al.

(10) Patent No.: US 11,447,457 B2
(45) Date of Patent: Sep. 20, 2022

(54) METHODS AND SYSTEMS FOR TREATMENT OF ETHYLENE OXIDE

(71) Applicant: Novomer, Inc., Boston, MA (US)

(72) Inventors: Konstantin A. Pokrovski, Boston, MA (US); John B. Ruhl, Boston, MA (US); Alexander Tseitlin, Boston, MA (US); Kyle Sherry, Boston, MA (US)

(73) Assignee: Novomer, Inc., Rochester, NY (US)

( * ) Notice: Subject to any disclaimer, the term of this patent is extended or adjusted under 35 U.S.C. 154(b) by 0 days.

(21) Appl. No.: 16/479,530

(22) PCT Filed: Jan. 18, 2018

(86) PCT No.: PCT/US2018/014243
§ 371 (c)(1),
(2) Date: Jul. 19, 2019

(87) PCT Pub. No.: WO2018/136638
PCT Pub. Date: Jul. 26, 2018

(65) Prior Publication Data
US 2019/0359581 A1 Nov. 28, 2019

Related U.S. Application Data

(60) Provisional application No. 62/448,337, filed on Jan. 19, 2017.

(51) Int. Cl.
*C07D 301/32* (2006.01)
(52) U.S. Cl.
CPC .................................. *C07D 301/32* (2013.01)

(58) Field of Classification Search
CPC .................................................... C07D 301/32
USPC ............................................................. 549/513
See application file for complete search history.

(56) References Cited

U.S. PATENT DOCUMENTS

| | | |
|---|---|---|
| 3,418,338 A | 12/1968 | Gilman |
| 4,221,727 A | 9/1980 | Tsang et al. |
| 6,123,812 A | 9/2000 | Bessling et al. |
| 6,348,611 B1 | 2/2002 | Lee et al. |
| 8,277,660 B2 | 10/2012 | Kimball et al. |
| 2006/0189833 A1 | 8/2006 | Powell et al. |
| 2009/0287280 A1 | 11/2009 | Wong et al. |
| 2014/0221702 A1 | 8/2014 | Weston et al. |

OTHER PUBLICATIONS

Written Opinion of the International Searching Authority for co-pending International Application No. PCT/US2018/014243 dated Mar. 28, 2018 (7 pages).
International Preliminary Report on Patentability in co-pending International Application No. PCT/US2018/014243 dated Jul. 23, 2019 (8 pages).
International Search Report on co-pending International Application No. PCT/US2018/014243 dated Mar. 28, 2018 (3 pages).

*Primary Examiner* — Taylor V Oh
(74) *Attorney, Agent, or Firm* — Young Basile Hanlon & MacFarlane, P.C.

(57) ABSTRACT

Disclosed are methods for treating an ethylene oxide stream suitable for use in carbonylation reactions. Such treatment uses an inorganic solid to remove water from the ethylene oxide stream. Discloses are also systems to carry out the methods herein.

12 Claims, No Drawings

METHODS AND SYSTEMS FOR TREATMENT OF ETHYLENE OXIDE

CROSS REFERENCE TO RELATED APPLICATIONS

This application is a U.S. National Phase Patent Application under 35 U.S.C. § 371 of International Application No. PCT/US2018/014243, filed Jan. 18, 2018, which claims priority to and the benefit of U.S. Provisional Patent Application No. 62/448,337, filed on Jan. 19, 2017, each of which is hereby incorporated by reference in its entirety.

FIELD

The present disclosure relates generally to the treatment of ethylene oxide, and more specifically to methods and systems for treatment of ethylene oxide for use in carbonylation reactions.

BACKGROUND

Ethylene oxide can be combined with carbon monoxide in the presence of a carbonylation catalyst to form beta-propiolactone or succinic anhydride. These products can be converted to C3 and C4 commodity chemicals, such as glacial acrylic acid, tetrahydrofuran (THF) and 1,4-butanediol. Access to these products depends, in part, on cabonylating ethylene oxide on a commercial scale. Various challenges are known in the art regarding the handling of ethylene oxide on a commercial scale. Thus, what is desired in the art are methods of treating ethylene oxide suitable for use in carbonylation reactions.

BRIEF SUMMARY

Provided herein are methods and systems that involve the treatment of an ethylene oxide feed suitable for use in carbonylation reactions. In some aspects, provided is a method of treating ethylene oxide, which includes:
  wetting a water-removing solid with organic solvent, or ethylene oxide, or a combination thereof; and
  continuously contacting the wetted water-removing solid with an ethylene oxide feed to produce a treated ethylene oxide stream,
    wherein the ethylene oxide feed includes ethylene oxide and has an initial water content, the treated ethylene oxide stream includes ethylene oxide and has a water content, and the water content of the treated ethylene oxide stream is lower than the initial water content; and
    the contacting of the wetted water-removing solid with the ethylene oxide feed produces heat, wherein the heat produced is less than is produced when contacting a non-wetted water-removing solid with an ethylene oxide feed.

In some aspects, provided is a method of continuously providing ethylene oxide to a carbonylation zone, which includes:
  wetting a water-removing inorganic solid with organic solvent, ethylene oxide, or a combination thereof;
  continuously contacting the wetted water-removing inorganic solid with an ethylene oxide feed to produce a treated ethylene oxide stream;
  feeding the treated ethylene oxide stream to a carbonylation zone; and
  contacting the treated ethylene oxide stream with carbon monoxide in the presence of a carbonylation catalyst in the carbonylation zone,
    wherein the ethylene oxide feed has an initial water content, the treated ethylene oxide stream has a water content, and the water content of the treated ethylene oxide stream is lower than the initial water content; and
    the contacting produces heat, wherein the heat produced is less than is produced when contacting a non-wetted water-removing inorganic solid with an ethylene oxide feed.

In some variations, contacting the treated ethylene oxide stream with carbon monoxide in the presence of a carbonylation catalyst in the carbonylation zone produces a carbonylation product which may include beta-propiolactone, succinic anhydride, or a mixture thereof.

In yet another aspect, provided herein is a system for treatment of ethylene oxide, which includes:
  an ethylene oxide source configured to provide an ethylene oxide feed; and
  a water removal unit comprising an inlet configured to receive the ethylene oxide feed, an outlet configured to output a treated ethylene oxide stream, and a wetted water-removing solid,
    wherein the water removal unit is configured to contact the ethylene oxide feed with the wetted water-removing solid;
    the wetted water-removing solid is wetted with organic solvent, ethylene oxide, or a mixture thereof;
    the ethylene oxide feed comprises ethylene oxide and has an initial water content, the treated ethylene oxide stream comprises ethylene oxide and has a water content, and the water content of the treated ethylene oxide stream is lower than the initial water content; and
    the contacting produces heat, wherein the heat produced is less than is produced when contacting a non-wetted water-removing solid with an ethylene oxide feed.

In still another aspect, provided herein is a system for continuously providing ethylene oxide to a carbonylation zone, which includes:
  an ethylene oxide source configured to provide an ethylene oxide feed;
  a water removal unit comprising an inlet configured to receive the ethylene oxide feed, an outlet configured to output a treated ethylene oxide stream, and a wetted water-removing solid,
    wherein the water removal unit is configured to contact the ethylene oxide feed with the wetted water-removing solid;
    the wetted water-removing solid is wetted with organic solvent, ethylene oxide, or a mixture thereof;
    the ethylene oxide feed comprises ethylene oxide and has an initial water content, the treated ethylene oxide stream comprises ethylene oxide and has a water content, and the water content of the treated ethylene oxide stream is lower than the initial water content; and
    the contacting produces heat, wherein the heat produced is less than is produced when contacting a non-wetted water-removing solid with an ethylene oxide feed; and
  a carbonylation zone comprising an inlet configured to receive the treated ethylene oxide stream, wherein the carbonylation zone is configured to contact the treated ethylene oxide stream with carbon monoxide in the presence of a carbonylation catalyst.

In some variations, contacting of the treated ethylene oxide stream with carbon monoxide in the presence of a carbonylation catalyst produces a carbonylation product which may include beta-propiolactone, succinic anhydride, or combination thereof.

In some variations of the foregoing methods, the treated ethylene oxide stream has a water content at least 50% lower than the initial water content. In other variations, the initial water content is above 5 ppm, or the water content of the treated ethylene oxide stream is less than 2 ppm, or both. In certain variations, contacting the wetted water-removing solid with the ethylene oxide feed results in less than 10 wt % of the ethylene oxide polymerizing, or less than 10 wt % of the ethylene oxide being converted to ethylene glycol. In certain variations, the organic solvent includes an ether, such as tetrahydrofuran.

DETAILED DESCRIPTION

Provided herein are methods of treating an ethylene oxide feed suitable for use in carbonylation reactions. The presence of water in ethylene oxide can result in a variety of negative effects in continuous carbonylation processes. Methods of removing water from ethylene oxide may include the use of water-removing solids, such as molecular sieves, to remove trace water. However, contacting water-removing solids with ethylene oxide can be exothermic, producing heat which may lead to homopolymerization of ethylene oxide and/or reaction of ethylene oxide with water. These side reactions may reduce carbonylation yields, and the side products can impact the efficient operation of commercial-scale continuous processes. Thus, provided herein are methods of removing excess water from ethylene oxide, while controlling such side reactions.

In some aspects, provided are methods of treating an ethylene oxide feed with a water-removing solid to produce a treated ethylene oxide feed. In certain embodiments, contacting ethylene oxide with a water-removing solid, such as molecular sieves, may result in the conversion of ethylene oxide to side products, such as poly(ethylene glycol) and/or ethylene glycol. Without wishing to be bound by any theory, an increase in temperature during the initial contact of ethylene oxide with a water-removing solid may result in localized heating, which can promote side reactions that include, for example, polymerization of ethylene oxide to produce poly(ethylene glycol), and/or reaction of ethylene oxide with water.

In some variations, the methods include controlling the contact conditions between an ethylene oxide feed and a water-removing solid, such that, compared to if the conditions were not controlled, the amount of heat generated is decreased, a lower ethylene oxide feed temperature is achieved, or there is a reduction in undesirable side reactions, or any combinations thereof.

In certain aspects, provided herein are methods of wetting a water-removing solid, and then contacting an ethylene oxide feed with the wetted water-removing solid to produce a treated ethylene oxide stream. In other aspects, contacting an ethylene oxide feed with a wetted water-removing solid produces less heat, maintains a lower ethylene oxide temperature, and/or reduces ethylene oxide side reactions, as compared to contacting an ethylene oxide feed with a non-wetted water-removing solid. The treated ethylene oxide stream may undergo further processes, such as carbonylation to produce beta-propiolactone and/or succinic anhydride.

In other aspects, provided are systems of contacting an ethylene oxide feed with a wetted water-removing solid to produce a treated ethylene oxide stream. These methods and the systems are described in further detail below.

Methods of Treating Ethylene Oxide Feed

As described above, in some aspects, the methods described herein include controlling the contact conditions between the ethylene oxide feed and the water-removing solid such that the amount of heat generated is decreased, a lower ethylene oxide temperature is achieved, and/or there is a reduction in undesirable side reactions, as compared to if the conditions were not controlled. As used herein, ethylene oxide may also be referred to as "EO".

In certain embodiments, the methods described herein include controlling the contact conditions between an ethylene oxide feed and a water-removing solid such that the temperature of the ethylene oxide in the feed remains within a certain range. In some variations, the ethylene oxide feed is contacted by a water-removing solid in an adsorber or drying bed, and controlling the contact conditions between the ethylene oxide feed and the water-removing solid results in the temperature of the ethylene oxide in the adsorber or drying bed remaining within a certain range. In some embodiments, controlling the contact conditions between an ethylene oxide feed and a water-removing solid reduces undesired side reactions, such as, for example, polymerization of ethylene oxide and/or reaction of ethylene oxide with water to produce ethylene glycol.

Wetting the Water-Removing Solid

Methods of controlling the contact conditions may include, for example, wetting the water-removing solid prior to contact with the ethylene oxide feed. The water-removing solid may be wetted with, for example, a solvent, ethylene oxide, or a combination thereof, prior to contact with the ethylene oxide feed. In certain embodiments, the methods are characterized in that the ethylene oxide feed is not brought into contact with unwetted water-removing solid.

It should be understood that the solvent, ethylene oxide, or combination thereof used to wet the water-removing solid may, in some embodiments, contain no water, or contain only trace amounts of water. Thus, the water-removing solid may be wetted with a non-aqueous solvent, non-aqueous ethylene oxide, or non-aqueous combination thereof.

Without being bound by any theory, wetting the water-removing solid with a solvent prior to contacting the ethylene oxide feed or prior to establishing a continuous ethylene oxide feed may reduce the amount of heat generated by the contact, the temperature of the ethylene oxide feed, and/or the amount of unwanted side products produced relative to the use of non-wetted water-removing solid. Thus, the use of wetted water-removing solid may, in some embodiments, allow water to be removed from the ethylene oxide feed while controlling the heat and/or side products generated. This may increase carbonylation yield in optional downstream processes, such as carbonylation of ethylene oxide to produce succinic anhydride, beta-propiolactone, or a combination thereof.

Wetting the water-removing solid may include contacting the water-removing solid with a solvent, ethylene oxide, or a combination thereof until the surface of the solid is saturated with solvent, ethylene oxide, or combination thereof.

In some variations, wetting the water-removing solid comprises saturating the external surfaces of the water-removing solid with the solvent, ethylene oxide, or combination thereof. In some variations, the water-removing solid comprises pores, and wetting the water-removing solid comprises saturating the surfaces within the pores. In still other variations, the water-removing solid comprises particles and pores, and in some embodiments wetting the water-removing solid comprises having solvent, ethylene oxide, or a combination thereof present between the particles, within the pores, or a combination thereof.

In some embodiments, excess solvent is removed prior to contacting the wetted water-removing solid with the ethylene oxide feed or prior to establishing a continuous ethylene oxide feed, while in other embodiments the excess solvent is not removed. It should be understood that when excess solvent is removed, solvent may still be present on the external surfaces, surfaces within the pores (if present), between particles (if present), and within pores (if present) of the water-removing solid.

In some embodiments, the water-removing solid is wetted with ethylene oxide. This may be done by gradually introducing ethylene oxide to the water-removing solid while maintaining the temperature of the ethylene oxide within a specified range. In some embodiments, the ethylene oxide is gaseous, while in other embodiments the ethylene oxide is liquid. In some embodiments, the ethylene oxide is introduced to the water-removing solid as a mixture, for example as a combination of ethylene oxide an inert gas, or a combination of ethylene oxide and a solvent.

In certain embodiments, contacting an ethylene oxide feed with a wetted water-removing solid leads to at least 99% lower, at least 90% lower, at least 80% lower, at least 70% lower, at least 60% lower, at least 50% lower, at least 40% lower, at least 30% lower, at least 20% lower, at least 10% lower, at least 5% lower, at least 1% lower, between 1% and 99% lower, between 10% and 90% lower, between 10% and 50% lower, between 1% and 10% lower, or between 1% and 20% lower polymerization of ethylene oxide than if the ethylene oxide feed were contacted with a water-removing solid that was not wetted.

In certain embodiments, contacting an ethylene oxide feed with a wetted water-removing solid leads to at least 99% lower, at least 90% lower, at least 80% lower, at least 70% lower, at least 60% lower, at least 50% lower, at least 40% lower, at least 30% lower, at least 20% lower, at least 10% lower, at least 5% lower, at least 1% lower, between 1% and 99% lower, between 10% and 90% lower, between 10% and 50% lower, between 1% and 10% lower, or between 1% and 20% lower conversion of ethylene oxide to ethylene glycol than if the ethylene oxide feed were contacted with a water-removing solid that was not wetted.

In certain embodiments, contacting an ethylene oxide feed with a wetted water-removing solid produces at least 99% less, at least 90% less, at least 80% less, at least 70% less, at least 60% less, at least 50% less, at least 40% less, at least 30% less, at least 20% less, or at least 10% less heat than is produced by contacting a non-wetted water-removing solid with an ethylene oxide feed.

In certain embodiments, contacting an ethylene oxide feed with a wetted water-removing solid results in less than 15 wt %, less than 10 wt %, less than 5 wt %, less than 1 wt %, less than 0.5 wt %, or less than 0.1 wt % of the ethylene oxide polymerizing.

In certain embodiments, contacting an ethylene oxide feed with a wetted water-removing solid results in less than 15 wt %, less than 10 wt %, less than 5 wt %, less than 1 wt %, less than 0.5 wt %, or less than 0.1 wt % of the ethylene oxide being converted to ethylene glycol.

Suitable solvents for wetting the water-removing solid may include, for example, hydrocarbons, ethers, esters, nitriles, or sulfones, or any mixtures thereof. In certain embodiments, the water-removing solid is wetted with a solvent comprising an ether. In certain embodiments, the ether is selected from the group consisting of tetrahydrofuran, 1,4-dioxane, glyme, diglyme, triglyme, tetraglyme, diethyl ether, diphenyl ether, methy-t-butyl ether, and any combinations thereof. In certain embodiments, the ether comprises tetrahydrofuran. In certain embodiments, the ether comprises 1,4-dioxane. In certain embodiments, the ether comprises diglyme. In certain embodiments, the solvent used to wet the water-removing solid is the same solvent used in one or more downstream processes, such as optional carbonylation of the treated ethylene oxide stream. In other embodiments, the ethylene oxide feed contacting the water-removing solid comprises a solvent, wherein the solvent is the same solvent used to wet the water-removing solid.

Contact Temperature

In some embodiments, controlling the contact conditions between the ethylene oxide feed and the water-removing solid includes contacting the ethylene oxide feed with the water-removing solid at a temperature that does not lead to polymerization, or leads to lower polymerization than contact at a different temperature. In one embodiment, the ethylene oxide feed is contacted with a water-removing solid at a temperature of less than 100° C., less than 70° C., or less than 50° C. In certain embodiments, contacting the ethylene oxide feed with a water-removing solid at a temperature less than 100° C., less than 70° C., or less than 50° C. leads to at least 99% lower, at least 90% lower, at least 80% lower, at least 70% lower, at least 60% lower, at least 50% lower, at least 40% lower, at least 30% lower, at least 20% lower, at least 10% lower, at least 5% lower, at least 1% lower, between 1% and 99% lower, between 10% and 90% lower, between 10% and 50% lower, between 1% and 10% lower, or between 1% and 20% lower polymerization of ethylene oxide than if the ethylene oxide feed were contacted with the water-removing solid at a higher temperature.

In certain embodiments, the step of contacting the ethylene oxide feed with the water-removing solid is maintained within the range of about −20° C. to about 70° C., from about −15° C. to about 40° C., from about −10° C. to about 30° C., from about −10° C. to about 20° C., from about −20° C. to about 0° C., from about 10° C. to about 20° C., or from about 10° C. to about 50° C.

In other embodiments, the methods and processes described herein include controlling the contact conditions between the ethylene oxide stream and the water-removing solid such that contacting the ethylene oxide stream with the water-removing solid increases the temperature of the ethylene oxide stream by less than 10° C., 5° C., less than 4° C., less than 3° C., less than 2° C., less than 1° C., less than 0.5° C., or less than 0.1° C.

Water-Removing Solid

In certain embodiments, the water-removing solid adsorbs water. In some embodiments, the water-removing solid is an inorganic solid. In some embodiments, the water-removing solid is a zeolite, a porous glass composition, a clay, or a silica. In some embodiments, the water-removing solid comprises a molecular sieve.

In certain embodiments, the water-removing solid comprises a molecular sieve having a pore size too small to effectively admit ethylene oxide molecules. In some embodiments, the pore size is less than 4.2 Å.

In certain embodiments, the water-removing solid is a molecular sieve, wherein the molecular sieve has a pore size less than 4.2 Å, less than 4.0 Å, less than 3.8 Å, less than 3.6 Å, less than 3.4 Å, less than 3.2 Å, or less than 3.0 Å. In certain embodiments, the water-removing solid is a molecular sieve, wherein the molecular sieve has a pore size of 3 Å, or of 4 Å. In certain embodiments, the water-removing solid comprises a molecular sieve, wherein the molecular sieve has a mixture of pore sizes. In certain embodiments, the molecular sieve comprises a microporous inorganic solid. In certain embodiments, the molecular sieve comprises a zeolite.

In other variations, any combinations of the water-removing solids described herein may be used.

Ethylene Oxide Feed

The ethylene oxide feed comprises ethylene oxide, and may be liquid, gaseous, or a combination thereof. In certain embodiments, the ethylene oxide feed comprises an initial water content, and contacting the ethylene oxide feed with a water-removing solid produces a treated ethylene oxide stream which has a water content lower than the initial water content of the ethylene oxide feed.

Water Content

In certain embodiments, the ethylene oxide feed has an initial water content above 20 ppm, above 10 ppm, above 5 ppm, or above 1 ppm. In some embodiments, the water content of the treated ethylene oxide stream is less than 20 ppm, less than 15 ppm, less than 10 ppm, less than 5 ppm, less than 4 ppm, less than 3 ppm, less than 2 ppm, or less than 1 ppm. In certain embodiments, the water content of the treated ethylene oxide stream is less than 0.5 ppm, less than 0.4 ppm, less than 0.25 ppm, less than 0.1 ppm, less than 0.05 ppm, or less than 0.01 ppm.

In certain embodiments, the ethylene oxide feed has an initial water content above 20 ppm, and the treated ethylene oxide stream has a water content of less than 10 ppm. In certain embodiments, the ethylene oxide feed has an initial water content above 10 ppm, and the treated ethylene oxide stream has a water content of less than 5 ppm.

In certain embodiments, the ethylene oxide feed has an initial water content between about 100 ppm and about 500 ppm, between about 20 ppm and about 200 ppm, between about 4 ppm and about 200 ppm, between about 20 ppm and about 100 ppm, between about 4 ppm and about 100 ppm, and the water content of the treated ethylene oxide stream is less than 10 ppm, less than 5 ppm, less than 2 ppm, or less than about 1 ppm.

In some embodiments, the treated ethylene oxide stream has a water content at least 50% lower, at least 40% lower, at least 30% lower, at least 20% lower, or at least 10% than the initial water content of the ethylene oxide stream.

Feed Composition

In some embodiments, the ethylene oxide feed comprises between 1% and 99% ethylene oxide by weight, between 2% and 90% ethylene oxide by weight, between 5% and 80% ethylene oxide by weight, between 5% and 70% ethylene oxide by weight, between 5% and 75% ethylene oxide by weight, between 10% and 90% ethylene oxide by weight, between 20% and 80% ethylene oxide by weight, between 20% and 70% ethylene oxide by weight, between 30% and 40% of ethylene oxide by weight, or between 40% and 75% ethylene oxide by weight.

In certain embodiments, the ethylene oxide feed comprises a solvent. Suitable solvents may include, for example, hydrocarbons, ethers, esters, nitriles, or sulfones, or any mixtures thereof. In certain embodiments, the ethylene oxide feed comprises ethylene oxide and an ether. In some embodiments, the ether is selected from the group consisting of tetrahydrofuran, 1,4-dioxane, glyme, diglyme, triglyme, tetraglyme, diethyl ether, diphenyl ether, methy-t-butyl ether, and any mixtures thereof. In certain embodiments, the ether comprises tetrahydrofuran. In certain embodiments, the ether comprises 1,4-dioxane. In certain embodiments, the ether comprises diglyme.

Contacting the Ethylene Oxide Feed with Water-Removing Solid

In certain embodiments, the step of contacting the ethylene oxide feed with a water-removing solid comprises continuously flowing the ethylene oxide feed through a fixed bed comprising the water-removing solid. In certain embodiments, the step of contacting the ethylene oxide feed with a water-removing solid comprises continuously flowing the ethylene oxide feed through one or more vessels containing a slurry of the water-removing solid. In certain embodiments, the ethylene oxide feed is in contact with the water-removing solid between about 0.5 and about 240 minutes. In certain embodiments, the time the ethylene oxide feed is in contact with the water-removing solid is sufficient for the initial water content in the ethylene oxide feed to be reduced by at least 50%, by at least 75%, by at least 85%, by at least 95%, by at least 95%, by at least 98%, or by at least 99%. In certain embodiments, the time the ethylene oxide feed is in contact with the water-removing solid is sufficient for the initial water content in the ethylene oxide feed to be reduced by at least 5%, by at least 10%, by at least 20%, by at least 30%, or by at least 40%.

In certain embodiments, the methods or systems described herein comprise two or more columns (or slurry beds) of the water-removing solid. This may allow, for example, the gaseous or liquid ethylene oxide feed to be flowed through a first column comprising the water-removing solid for a first interval, then the flow may be diverted to a second column comprising water-removing solid for a second interval. The flow may be diverted again for subsequent columns, for example in a system or method using three, four, five, six, or more columns (or slurry beds). In certain embodiments, a column comprising the water-removing solid is contacted by the ethylene oxide stream for a period of time, the ethylene oxide stream is diverted to one or more subsequent columns, the water-removing solid in the first column is regenerated, and the regenerated column is again contacted by the ethylene oxide stream. Regeneration of the water-removing solid may include draining liquid from the water-removing solid, displacing any residual ethylene oxide with ambient nitrogen, and then heating the water-removing solid to a temperature from 150° C. to 250° C. under reduced pressure (e.g., a vacuum) or under a flow of inert gas (e.g., nitrogen).

In certain embodiments, the method includes determining the efficiency of the water removal to determine when to switch the ethylene oxide feed to a subsequent column. This may include, for example, analyzing the water content of the treated ethylene oxide stream exiting one or more columns and diverting the stream to one or more subsequent columns when the water content of the treated ethylene oxide stream exceeds a certain threshold. In other embodiments, determining the water removal efficiency may include determining the amount of water absorbed by a column (or group of columns) and comparing this value to a certain threshold for absorption capacity of that column (or group of columns). For example, the water content of the treated ethylene oxide stream may be quantified and compared to the water content of the ethylene oxide feed, and the amount of water absorbed by the column calculated by totalizing the flow rate of ethylene oxide over time.

Systems for Ethylene Oxide Treatment

In another aspect, provided are systems for treatment of an ethylene oxide feed. In some embodiments, the system includes an ethylene oxide source configured to provide an ethylene oxide feed; and a water removal unit comprising an inlet configured to receive the ethylene oxide feed, an outlet configured to output a treated ethylene oxide stream, and a wetted water-removing solid. In some variations, the system further comprises a monitoring unit configured to monitor the water content of the treated ethylene oxide stream.

It should be understood that any of the variations described above for the methods provided apply to the systems described herein. For example, the systems described herein are configured to receive and use the variations of the water-removing solid and the ethylene oxide feed, and treat the ethylene oxide feed In certain embodiments, the water removal unit is configured to contact the ethylene oxide feed with the wetted water-removing solid. In other embodiments, the wetted water-removing solid is wetted with organic solvent, ethylene oxide, or a mixture thereof. The ethylene oxide feed comprises ethylene oxide and has an initial water content, and the treated ethylene oxide stream comprises ethylene oxide and has a water content. In some embodiments, the water content of the treated ethylene oxide stream is lower than the initial water content. As described above, contacting the ethylene oxide feed produces heat, and in some embodiments, the systems described herein are configured so that the heat produced is less than would be produced when contacting a non-wetted water-removing solid with an ethylene oxide feed.

In certain embodiments, the ethylene oxide source is configured to continuously provide an ethylene oxide feed to the inlet of the water removal unit.

In some embodiments, the ethylene oxide feed entering the water removal unit is at a temperature that does not lead to, or minimizes, the homopolymerization of ethylene oxide upon contacting the water-removing solid. In one embodiment, the ethylene oxide feed enters the water removal unit at a temperature less than 100° C., less than 70° C., or less than 50° C.

In certain embodiments, the temperature of the water removal unit is between about 20° C. to about 70° C., from about −15° C. to about 40° C., from about −10° C. to about 30° C., from about −10° C. to about 20° C., from about −20° C. to about 0° C., from about 10° C. to about 20° C., or from about 10° C. to about 50° C.

As described above, the ethylene oxide feed comprises ethylene oxide and optionally a solvent. In some embodiments, the solvent comprises an ether. In certain embodiments, the ether is selected from the group consisting of tetrahydrofuran, 1,4-dioxane, glyme, diglyme, triglyme, tetraglyme, diethyl ether, diphenyl ether, methy-t-butyl ether, and any combinations thereof. In certain embodiments, the ether comprises tetrahydrofuran. In certain embodiments, the ether comprises 1,4-dioxane. In certain embodiments, the ether comprises diglyme. In certain embodiments, the ethylene oxide feed comprises a solvent, wherein the same solvent is used in one or more downstream processes, such as carbonylation of ethylene oxide to produce beta-propiolactone, succinic anhydride, or a combination thereof.

The ethylene oxide feed entering the inlet of the water removal unit may comprise between 10 wt % and 90 wt % ethylene oxide, between 20 wt % and 80 wt % ethylene oxide, between 20 wt % and 70 wt % ethylene oxide, between 30 wt % and 40 wt % ethylene oxide, or between 40 wt % and 75 wt % ethylene oxide. In certain embodiments, the weight percent of ethylene oxide in the ethylene oxide feed is between 1 wt % and 99 wt %, between 2 wt % and 90 wt %, between 5 wt % and 80 wt %, between 5 wt % and 70 wt %, or between 5 wt % and 75 wt %.

In certain embodiments, the water removal unit is configured to continuously flow the ethylene oxide feed through a contact zone where it contacts the wetted water-removing solid. In certain embodiments, the water removal unit comprises one or more fixed beds or one or more slurry beds comprising the water-removing solid. In certain embodiments, the mean time between the ethylene oxide feed entering the water removal unit from the ethylene oxide source and the treated ethylene oxide stream exiting the water removal is between about 0.5 and about 240 minutes. In certain embodiments, the time ethylene oxide feed is in contact with the water-removing solid is sufficient for the initial water content in the entering ethylene oxide feed to be reduced by at least 50%, at least 75%, at least 85%, at least 95%, at least 95%, at least 98%, or at least 99%.

In certain embodiments, the water removal unit comprises two or more parallel treatment zones, and is configured to switch the flow of the ethylene oxide feed from a first treatment zone (or group of treatment zones) to another parallel treatment zone (or group of treatment zones). It should be understood that each treatment zone may comprise one or more columns or reactors (or combinations of columns and reactors). Where two or more columns or reactors are present in a treatment zone they may be arrayed in parallel, in series, or any combination of parallel and series.

In certain embodiments, the system further comprises a monitoring unit. In some variations, the monitoring unit is configured to monitor the water content of the treated ethylene oxide stream, the initial water content of the ethylene oxide feed, or a combination thereof. This may include, for example, monitoring the water content of the treated ethylene oxide stream exiting one or more columns in a water removal unit.

In some variations, the monitoring unit is configured to monitor the amount of water removed by the water removal unit, or to monitor the efficiency of the water removal unit.

In some embodiments, the water content, amount of water, or efficiency monitored by the monitoring unit is compared to a threshold value. In some embodiments, the threshold value is 5 ppm water, 3 ppm water, 10 wt % water, or 5 wt % water. For example, in some embodiments a monitoring apparatus monitors the amount of water removed by the water removal unit, and this amount is compared to a threshold value of 10 wt % water, or 5 wt % water. In some embodiments, a monitoring apparatus monitors the water content of the treated ethylene oxide stream, and this content is compared to a threshold value of 5 ppm water, or 3 ppm water.

In some embodiments, when the water content of the treated ethylene oxide stream, amount of water removed by the water removal unit, or efficiency of the water removal unit approaches a threshold value, the ethylene oxide feed is switched from a first treatment zone to a parallel treatment zone. Thus, in some embodiments, the system further comprises an apparatus to switch the ethylene oxide feed from a first treatment zone to another parallel treatment zone. The water content of the treated ethylene oxide stream or amount of water removed by the water removal unit may be maintained below a certain threshold value, or the efficiency of the water removal unit may be maintained above a certain threshold value, by monitoring with the monitoring unit as described above and switching the ethylene oxide feed from a first treatment zone to a parallel treatment zone when nearing the threshold value.

For example, in some embodiments the system comprises a monitoring unit to measure the efficiency of the water removal unit, and an apparatus to switch the ethylene oxide feed from a first treatment zone to another parallel treatment zone such that the efficiency of the water removal stage can be maintained above a desired threshold value.

In certain embodiments, the system further comprises a regeneration unit for regenerating one or more treatment zones while another parallel treatment zone is in use. In certain embodiments, the system comprises apparatus for purging a treatment zone of ethylene oxide prior to regeneration of the water-removing solid. Purging may be desirable to prevent reactions of residual ethylene oxide during regeneration and to mitigate hazards associated with heating ethylene oxide vapor. In certain embodiments, the purging apparatus includes a vacuum source that can be coupled to the treatment zone to be regenerated. In some embodiments, the purging apparatus includes a source of inert gas such as nitrogen or argon that can be coupled to the treatment zone to be regenerated and optionally an outlet for the inert gas to exit the treatment zone being regenerated. In certain embodiments, the purging apparatus comprises a vacuum source, an inert gas source, and a manifold to affect alternate coupling of each to the treatment zone to be regenerated. In certain embodiments, the system comprises scrubbing apparatus for capture or destruction of ethylene oxide purged from the treatment zone by operation the purging apparatus. In certain embodiments, scrubbing apparatus are coupled to the exhaust of the vacuum source and/or to an inert gas outlet from the purging apparatus. Scrubbing apparatus may include, for example, aqueous scrubbing baths, reactive resins, thermal oxidizers, flares, or combinations thereof. Regeneration of the treatment zones may include, for example, application of heat and/or vacuum and/or flow of an inert gas or fluid through the treatment zone.

In some embodiments, the system further comprises a carbonylation zone comprising an inlet configured to receive the treated ethylene oxide stream. This carbonylation zone is, in certain embodiments, configured to contact the treated ethylene oxide stream with carbon monoxide in the presence of a carbonylation catalyst. In some embodiments, contacting the treated ethylene oxide stream with carbon monoxide in the presence of a carbonylation catalyst produces a carbonylation product comprising beta-propiolactone, succinic anhydride, or combination thereof.

EXAMPLES

The following Examples are merely illustrative and are not meant to limit any aspects of the present disclosure in any way.

Example 1

Continuous Drying of an EO Feed Stream for an EO Carbonylation Process Utilizing Online Water Measurement for Control An ethylene oxide input is supplied via pipeline from a co-located ethylene oxidation unit, where the ethylene oxide stream has an average water content between 10 ppm and 40 ppm. Prior to entering a downstream EO carbonylation reactor, the ethylene oxide feed is pumped into a water removal stage comprising six parallel jacketed, packed bed columns each containing 10,000 kg of zeolite-based 3 Å molecular sieves. Prior to start-up, each of the columns is filled with anhydrous tetrahydrofuran, and then the tetrahydrofuran is drained from the columns. At startup, two of the parallel columns are fed with liquid EO from the pipeline at a total flow rate of 10 metric tons/hr while the jackets of the active columns are connected to a flow of 10° C. cooling water. The water content of the outflow from each of the two columns is monitored by Karl Fischer titration. Water concentration over time in the two columns is monitored.

Once the water content of column 1 is found to exceed a predetermined threshold of 3 ppm, the EO feed to column 1 may be diverted to a new column that is recently regenerated. Column 1 is purged by alternate evacuation and flushing with nitrogen until an EO detector on the outlet registers less than 50 ppm EO in the nitrogen stream exiting the column during the flush. At this time, the jacket is drained of cooling liquid and a flow of 180° C. steam is introduced and maintained for 6 hour. The column is then cooled with aid of tempered water to the jacket, and dry tetrahydrofuran (THF) is flowed into the column from a THF feed tank that is part of the downstream carbonylation reactor. Once the column is filled with THF, it is maintained in this condition until it is needed to replace another exhausted column. This cycle is repeated continuously between the six columns to maintain a constant EO feedstream having less than 3 ppm water to the downstream carbonylation reactor.

Example 2

Continuous Drying of an EO Feed Stream for an EO Carbonylation Process Utilizing 4 Å Molecular Sieves This example follows the procedure described in Example 1, except the drying columns contain 4 Å molecular sieves.

Example 3

Continuous Drying of an EO Feed Stream for an EO Carbonylation Process Utilizing Higher Column Temperatures This example follows the procedure described in Example 1, except the drying columns are maintained at a temperature of 40-50° C. during operation.

Example 4

Continuous Drying of an EO Feed Stream for an EO Carbonylation Process Utilizing EO Solution as Feed This example follows the procedure described in Example 1, except the drying liquid EO stream fed to the EO inlet is a 50 wt % solution of EO in tetrahydrofuran.

Example 5

Continuous Drying of an EO Feed-Stream for an EO Carbonylation Process Utilizing Alternate Water Measurement Apparatus This example follows the procedure described in Example 1, except the water content of the EO feed-stream exiting the columns is monitored by mass spectroscopy.

Example 6

Drying of an EO Feed Stream for an EO Carbonylation Process Utilizing Pre-Wetted Molecular Sieves An EO drying column was fabricated from a 50 mL stainless steel cylinder with 7 micron welded filters, 41G series ball valves and appropriate fittings, all from Swagelok. The cylinder was packed with UOP EPG-2 molecular sieves (3 Å, 1/16" rods) which were subsequently activated in a flow of nitrogen (T=240° C.). The column with activated sieves was brought into a glove box and treated with dried THF (1 mL), to control heating upon addition of EO. The activated and treated sieve column was then connected to an EO cylinder and scrubbing system. Pre- and post-column EO samples were collected in a cylinder (3" length of ½" tubing fitted with a Swagelok cap, reducer and 41G ball valve). Before each collection, the sample cylinder was connected to a Schlenk line and evacuated to <100 mTorr while being heated to 100° C. After collection, a needle was connected to the valve of the sample cylinder while being purged with nitrogen. The cylinder/needle unit was quickly transferred from the nitrogen source to the inlet septum of a Karl-Fisher titrator (Mettler-Toledo C30), the needle inserted through the septum and the valve opened slowly to allow sample into the titrator. After each sample was titrated, the electrolyte (Fluka Hydranal Coulomat AG) was discarded, the cell washed with two 50 mL portions and filled with 100 mL of fresh electrolyte. The results are summarized in Table 1 below.

TABLE 1

Water concentration of EO sample taken before and after drying.

| Sample | Concentration of $H_2O$ in the sample (ppm) |
|---|---|
| Before drying | 20.9 |
| After drying | 10.5 |

What is claimed is:

1. A method of treating ethylene oxide, comprising:
    wetting a water-removing solid with organic solvent, or ethylene oxide, or a combination thereof; and
    continuously contacting the wetted water-removing solid with an ethylene oxide feed to produce a treated ethylene oxide stream,
    wherein the ethylene oxide feed comprises ethylene oxide and has an initial water content, the treated ethylene oxide stream comprises ethylene oxide and has a water content, and the water content of the treated ethylene oxide stream is lower than the initial water content, and
    wherein contacting the wetted water-removing solid with the ethylene oxide feed results in less than 10 wt % of the ethylene oxide polymerizing.

2. The method of claim 1, wherein the treated ethylene oxide stream has a water content at least 50% lower than the initial water content.

3. The method of claim 1, wherein:
   (i) the initial water content is above 5 ppm; or
   (ii) the water content of the treated ethylene oxide stream is less than 2 ppm; or both (i) and (ii).

4. The method of claim 1, wherein contacting the wetted water-removing solid with the ethylene oxide feed results in less than 10 wt % of the ethylene oxide being converted to ethylene glycol.

5. The method of claim 1, wherein the water-removing solid is a zeolite, clay, or silica, or any combinations thereof.

6. The method of claim 1, wherein the water-removing solid is a molecular sieve.

7. The method of claim 1, wherein contacting the water-removing solid with ethylene oxide comprises introducing ethylene oxide to the water-removing solid while maintaining the temperature of the ethylene oxide at less than 100 degrees Celsius.

8. The method of claim 1, wherein the organic solvent comprises an ether.

9. The method of claim 1, wherein the organic solvent comprises tetrahydrofuran, 1,4-dioxane, glyme, diglyme, triglyme, tetraglyme, diethyl ether, diphenyl ether, or methyt-butyl ether, or any combinations thereof.

10. The method of claim 1, wherein the organic solvent comprises tetrahydrofuran.

11. The method of claim 1, wherein the ethylene oxide feed is gaseous or liquid.

12. The method of claim 1, wherein the contacting the wetted water-removing solid with the ethylene oxide feed produces heat, wherein the heat produced is less than is produced when contacting a non-wetted water-removing solid with an ethylene oxide feed.

* * * * *